(12) United States Patent
Lance et al.

(10) Patent No.: US 7,795,263 B2
(45) Date of Patent: Sep. 14, 2010

(54) PHARMACEUTICAL COMBINATION FOR AND METHOD OF ANESTHETIZING AND IMMOBILIZING NON-DOMESTICATED MAMMALS

(75) Inventors: William R. Lance, Fort Collins, CO (US); Lisa L. Wolfe, Fort Collins, CO (US)

(73) Assignee: Wildlife Laboratories, Inc., Fort Collins, CO (US)

( * ) Notice: Subject to any disclaimer, the term of this patent is extended or adjusted under 35 U.S.C. 154(b) by 0 days.

(21) Appl. No.: 12/169,446

(22) Filed: Jul. 8, 2008

(65) Prior Publication Data

US 2010/0010006 A1  Jan. 14, 2010

(51) Int. Cl.
| | | |
|---|---|---|
| A61K 31/496 | (2006.01) | |
| A61K 31/44 | (2006.01) | |
| A01N 43/42 | (2006.01) | |
| A01N 43/50 | (2006.01) | |

(52) U.S. Cl. .................. 514/253.01; 514/282; 514/396
(58) Field of Classification Search ....................... None
See application file for complete search history.

(56) References Cited

U.S. PATENT DOCUMENTS

| | | | |
|---|---|---|---|
| 3,106,513 | A | 10/1963 | Reinhard |
| 4,544,664 | A | 10/1985 | Karjalainen et al. |
| 4,670,455 | A | 6/1987 | Virtanen et al. |
| 4,783,477 | A | 11/1988 | Lammintausta et al. |
| 4,910,214 | A | 3/1990 | Karjalainen et al. |
| 4,921,853 | A | 5/1990 | LeBlanc |
| 5,124,157 | A | 6/1992 | Colley et al. |
| 5,344,840 | A | 9/1994 | Maze et al. |
| 5,438,067 | A | 8/1995 | Jalonen et al. |
| 5,464,628 | A | 11/1995 | Jalonen et al. |
| 6,316,434 | B1 | 11/2001 | Robichaud et al. |
| 6,562,855 | B1 | 5/2003 | Franks et al. |
| 6,635,236 | B2 | 10/2003 | Bar |
| 6,716,867 | B1 | 4/2004 | Aantaa et al. |
| 6,770,678 | B1 * | 8/2004 | Kurz et al. .................. 514/634 |
| 7,001,609 | B1 | 2/2006 | Matson et al. |
| 2002/0068754 | A1 | 6/2002 | Olney et al. |
| 2003/0109447 | A1 | 6/2003 | Cupp et al. |
| 2003/0181354 | A1 | 9/2003 | Abdulrazik |
| 2005/0042194 | A1 | 2/2005 | Ng et al. |
| 2005/0177135 | A1 | 8/2005 | Hildebrand et al. |
| 2007/0116729 | A1 * | 5/2007 | Palepu .......................... 424/400 |
| 2007/0225602 | A1 | 9/2007 | Heaton et al. |
| 2008/0015210 | A1 | 1/2008 | Shah et al. |

OTHER PUBLICATIONS

Moresco et al., Journal of Zoo and Wildlife Medicine 34(4), 346-351, 2003.*

"Azaperone/Medetomidine/Fentanyl immobilization of Malayan Tapir," Utara, et al., Proceedings of AZWMP 2006, Chulalongkorn Uni. Fac. of Vet. Sc., Bangkok, Thailand, Oct. 26-29, 2006, p. 33, 1 page.
"Evaluation and testing of techniques for ungulate management," Thomas Lohuis, Alaska Department of Fish and Game, Division of Wildlife Conservation 2007, Research Annual Performance Report, Jul. 1, 2006-Jun. 30, 2007, Federal Aid in Wildlife Restoration, W-33-05, Project 1.63, published Sep. 30, 2007, 4 pages.
Ivis, "The Art and Science of Giraffe Immobilization/Anesthesia," Bush, et al., in Zoological Restraint and Anesthesia, D. Heard (Ed.), 6 pages. (Jan. 9, 2002).
"The cardiopulmonary effects of etorphine, azaperone, detomidine, and butorphanol in field-anesthetized white rhinoceroses," Wenger, et al., J. Zoological Wildlife Medicine, 38(3):380-7, Sep. 2007, 2 pages.
A Compendium of Drugs Used for Laboratory Animal Anesthesia, Analgesia, Tranquilization and Restraint, Drexel University, www.research.drexel.edu/forms/compliance/iacuc/IACUC_drugs.doc, 24 pages. (2002).
Guide to the Care and Use of Experimental Animals, vol. 1, 1993, Edited by Olfert, et al., Canadian Council on Animal Care, 1993, 16 pages.
Anaesthesia of the pig, Tore Framstad, Chapter 27, pp. 162-167, 6 pages. (2001).
"Medetomidine-butorphanol combination anesthesia in the dog," Guller, et al., Schweiz Arch Tierheilkd Dec. 2001; 143 (12):601-6; PMID: 11776718 [PubMed—indexed for MEDLINE], 1 page.
"Comparison of sedative effects induced by medetomidine, medetomidine-midazolam and medetomidine-butorphanol in dogs," Hayashi, et al., J. Veterinary Medical Science Oct. 1994; 56(5):951-6; PMID: 7865598 [PubMed—indexed for MEDLINE], 1 page.
"Comparative cardiovascular, analgesic, and sedative effects of medetomidine, medetomidine-hydromorphone, and medetomidine-butorphanol in dogs," Kuo, et al., American J. of Veterinary Research Jul. 2004; 65(7):931-7; PMID: 15281651 [PubMed—indexed for MEDLINE], 2 pages.
"Effects of intramuscular administration of low doses of medetomidine and medetomidine-butorphanol in middle-aged and old dogs," Muir, et al., J. American Veterinary Medical Association Oct. 15, 1999; 215(8):1116-20, PMID: 10530324 [PubMed—indexed for MEDLINE], 2 pages.
"Sedative and cardiorespiratory effects of medetomidine, medetomidine-butorphanol, and medetomidine-ketamine in dogs," Ko, et al., J. American Veterinary Medical Association May 15, 2000; 216(10):1578-83, PMID: 10825944 [PubMed—indexed for MEDLINE], 2 pages.

(Continued)

*Primary Examiner*—Brian-Yong S Kwon
*Assistant Examiner*—Bong-Sook Baek
(74) *Attorney, Agent, or Firm*—John R. Ley (57) ABSTRACT

Non-domesticated mammalian animals are anesthetized and immobilized by injecting an effective amount of an anesthetizing and immobilizing drug comprising pharmaceutically active ingredients of butorphanol tartrate, azaperone tartrate and medetomidine hydrochloride (BAM) into the animal from a dart. The BAM combination is preferably initially formed as lyophilized powder of the pharmaceutically active ingredients, and then reconstituted before injection as an injectable liquid in the environment of the animal.

16 Claims, 3 Drawing Sheets

OTHER PUBLICATIONS

Proceedings:Papers, Effects of Oil on Wildlife, 2007, edited by J. Gregory Massey, pp. 128-130, 7 pages.

"Enhancing effect of butorphanol on medetomidine-induced sedation in pigs," Sakaguchi, et al., J. Veterinary Medical Science Dec. 1992; 54(6):1183-5, PMID: 1477168 [PubMed—indexed for MEDLINE], 1 page.

"Cardiopulmonary Assessment of Medetomidine, Ketamine, and Butorphanol Anesthesia in Captive Thomson's Gazelles," Chittick, et al., Journal of Zoo and Wildlife Medicine, vol. 32, Issue 2, Jun. 2001, pp. 168-175, 2 pages.

"Surgical Management of Rectal Prolapse in an Indian Rhinoceros," Bertelsen, et al., Journal of Zoo and Wildlife Medicine 35(2):245-247, 2004, 3 pages.

"The sedative and analgesic effects of detomidine-butorphanol and detomidine alone in donkeys," Joubert, et al., J. South African Veterinary Association Sep. 1999; 70(3):112-8, PMID: 10852680 [PubMed —indexed for MEDLINE], 1 page.

"Standing Sedation in African Elephants Using Detomidine-Butorphanol Combinations," Neiffer, et al., Journal of Zoo and Wildlife Medicine, vol. 36, Issue 2, Jun. 2005, pp. 250-256, 2 pages.

"Anesthesia in a Baird's tapir," Trim, et al., J. of Zoological Wildlife Medicine Jun. 1998; 29(2):195-8, 9732036 (P,S,E,B), 4 pages.

"Butorphanol and Azaperone as a Safe Alternative for Repeated Chemical Restraint in Captive White Rhinoceros," Radcliffe, et al., Journal of Zoo and Wildlife Medicine 31(2):196-200, 2000, 5 pages.

"Intensive Management and Preventative Medicine Protocol for the Sumatran Rhinoceros," Radcliffe, et al., Internet, 18 pages. (2004).

"Successful treatment of a squamous cell carcinoma in a white rhinoceros," Goodman, et al., Veterinary Dermatology Dec. 2007; 18(6):460-3, 1 page.

"Standing laparoscopic-guided uterine biopsy in a southern white rhinoceros," Radcliffe, et al., J. Zoo Wildlife Medicine Jun. 2000; 31(2):201-7, 1 page.

"Use of Azaperone and Zuclopenthixol Acetate to Facilitate Translocation of White-Tailed Deer," Read, et al., Journal of Zoo and Wildlife Medicine, vol. 33, Issue 2, Jun. 2002, pp. 163-165, 2 pages.

IVIS, "Anesthesia of North American Deer," N. Caulkett, et al, Apr. 2, 2004, in Zoological Restraint and Anesthesia, D. Heard (Ed.), 8 pages.

"Medetomidine-Ketamine in Reindeer: Effective Immobilization by Hand- and Dart-Administered Injection," Ryeng, et al., Journal of Zoo and Wildlife Medicine, vol. 33, Issue 4, Dec. 2002, pp. 397-400, 1 page.

"Butorphanol Tartrate," The Elephant Formulary, Mikota, et al., Copyright 2003-06, Published by Elephant Care International, 7 pages.

"Azaperone (Adverse effect reported)," The Elephant Formulary, Mikota, et al., Copyright 2003-06, Published by Elephant Care International, 8 pages.

"Medetomidine HCl," The Elephant Formulary, Mikota, et al., Copyright 2003-06, Published by Elephant Care International, 4 pages.

"Detomidine HCl," The Elephant Formulary, Mikota, et al., Copyright 2003-06, Published by Elephant Care International, 4 pages.

"Medetomidine Hydrochloride," ZooPharm, Fort Collins, Colorado, 2 pages, (Jan. 4, 2006).

* cited by examiner

PHARMACEUTICAL COMBINATION FOR AND METHOD OF ANESTHETIZING AND IMMOBILIZING NON-DOMESTICATED MAMMALS

This invention relates to the anesthesia and immobilization of non-domesticated mammals, and more particularly to a new and improved anesthetizing and immobilizing pharmaceutical combination formed of the pharmaceutically active ingredients of butorphanol tartrate, azaperone tartrate and medetomidine hydrochloride (BAM), which is suitable for remote delivery by dart.

BACKGROUND OF THE INVENTION

Large non-domesticated mammals are typically anesthetized and immobilized for reasons of medical examination or treatment, or for reasons of physiologic or morphologic study or herd health assessment. Any such examination or study is impossible unless the animals are immobilized, because the non-domesticated nature of the animals makes it impossible to approach or safely handle them, even in captive environments such as zoological parks or animal preserves. Performing any procedure that may produce pain is also impossible unless the animals are anesthetized, because the animals will resist such procedures, even if the animals are substantially immobilized.

Because non-domesticated animals cannot be approached for injection by hand, it is necessary to remotely deliver an anesthetizing and immobilizing drug, typically from a single dart projected or shot from a gun at the distance which the animal will tolerate before fleeing, i.e. the flight distance. A dart is a syringe-like structure which has a drug-confining chamber and an attached hypodermic needle. When the dart impacts the animal, the hypodermic needle penetrates through the hair and hide of the animal and into muscle. An expulsion chamber containing compressed gas or a small explosive charge is activated upon impact and quickly forces the liquid anesthetizing and immobilizing drug from the drug-confining chamber through the needle into the muscle of the animal. The drug enters the bloodstream, and over a short time period anesthetizes and immobilizes the animal.

The flight distance which a non-domesticated animal will tolerate varies with the species and the environment. To accommodate lengthy flight distances, the dart should have a trajectory distance of about 70 meters with good accuracy. Any shorter range will not always be satisfactory because it is usually difficult or impossible to approach free ranging wildlife species any closer than approximately 35 meters. The trajectory range should permit sufficient accuracy to deliver the dart into the muscle mass of a shoulder or hind quarter of the animal, because impacting the dart with a bony area such as the rib cage or lower extremity will not allow the needle to penetrate adequately to deliver the full dose of the anesthetizing and immobilizing drug.

Increasing the velocity of a dart will increase its range and will contribute to its accuracy, but increased velocity of the dart increases the risk of excessive trauma or tissue wound to the animal from the impact of the dart. The risk of such a tissue wound is directly related to the kinetic energy of the dart, and the kinetic energy increases with the square of the velocity.

A dart injury in a free ranging animal is an ideal environment for clostridial species of anaerobic bacteria (the causative organisms of fatal clostridial septicemia) and other bacterial organisms to enter the blood circulatory system. The hair and hide of a free-ranging animal is a typical and natural environment for various organisms which are benign on the exterior of the animal, but which can be fatal upon entering the bloodstream. An example of such organisms are those which create tetanus (*Clostridium tetani*) clostridial septicemia or blackleg (*Clostridium chauvoei*), and anthrax (*Bacillus anthracis*). Such diseases may be fatal to the animal within 24 to 72 hours after entering the bloodstream. A high velocity impact from a dart creates a deep anaerobic protein rich environment conducive to the growth of these disease organisms. Therefore increasing the velocity of the dart is not usually an acceptable rationale to obtain improvements in range or accuracy. Excessive dart velocity can also result in fatal physical injury to the animal if it penetrates the thoracic cavity or into the internal organs of the abdominal cavity.

The weight of the dart also affects range and accuracy. A heavier weight dart will have less effective range than a lighter weight dart. The accuracy in placement of a heavier weight dart may be less than to a lighter weight dart, because the heavier dart may spend more time in trajectory and therefore fall more under the influence of gravity. A heavier dart will also create more tissue injury or trauma upon impact, resulting in more risk of disease from bacteria growth, as described above. The amount of tissue injury or trauma increases linearly with weight, rather than in relation to the square of the velocity.

One influence on the weight of the dart is the volume of the immobilizing and anesthetizing drug that it must carry. Larger volumes of the drug are heavier and require a larger dart. The weight and species of the non-domesticated animal contributes to the amount or volume of the immobilizing and anesthetizing drug that must be used. For example, an average adult white tailed deer (*Odocoileus virginianus*) weighs at least 50 kg, an average adult American black bear (*Ursus americanus*) may weigh 100-300 kg, an average adult moose (*Alces alces*) may weigh 200-300 kg, an adult North American elk (*Cervus elaphus*) may weigh 250-400 kg, and an average adult bison (*Bison bison*) may weigh 300-400 kg. Since a single dart must be effective in immobilizing and anesthetizing the animal, the dart must carry enough volume of the drug to achieve those effects. Although darts with a maximum capacity of about 5 or more ml are available, such darts are usually susceptible to the above described disadvantages of limited range and accuracy and excessive tissue injury. A dart with a drug-carrying capacity of 3 ml or less is preferred, because its reduced size usually avoids or minimizes the above described disadvantages.

Another factor which influences the volume of drug that the dart must carry is the potency of the anesthetizing and immobilizing drug. Combinations of drugs create synergistic anesthetic effects and allow lesser volumes to achieve greater effects in non-domesticated species. There are many different factors which influence the selections of the drugs in the combinations, such as the method of delivery, volume required, the duration and quality of the anesthesia, side effects, and the availability of antagonists for reversing the anesthetizing and immobilizing effect.

For example, xylazine, an alpha 2 adrenergic agonist, has been used to immobilize deer. Xylazine has also been combined with United States Drug Enforcement Agency (DEA) schedule II opioids such as etorphine or carfentanil, and has also been combined with DEA schedule III cyclohexamines such as ketamine and tiletamine, to synergistically improve efficacy and reduce drug volume. Medetomidine hydrochloride, another alpha 2 adrenergic agonist, has also been suggested as an alternative to xylazine, and has been tested in several deer species. Butorphanol tartrate, a morphine-based DEA schedule IV opioid, has been combined with medetomidine and xylazine for sedation of captive wildlife, but in so far as is known, butorphanol tartrate itself has been tested only as a post-surgical analgesic in deer. Azaperone tartrate, a neuroleptic sedative, has been combined with xylazine and/or fentanyl and with etorphine to immobilize deer but there are no known characterizations of the effects of the resulting anesthesia and immobilization.

Other potent opioid/alpha 2 agonist, opioid/alpha 2 agonist/dissociative anesthetic, opioid/alpha 2 agonist/neuroleptic tranquilizer, alpha 2 agonist/dissociative anesthetic and tiletamine/zolazepam combinations have also been used. Some of these drugs are reversible individually and in combination by the administration of antagonists.

Some of these synergistic drug combinations have been reported to create undesirable side effects, such as bloating and regurgitation, temperature regulation problems, hypoxemia, apnea/respiratory depression, hyperthermia, muscle rigidity, altered blood pressure, excitement, incomplete reversibility, and prolonged recovery times, among other things. These undesirable side effects occur despite achieving relatively adequate immobilization and anesthesia. As an example of the difficulties created by some of these undesirable side effects, any physical examination of an animal experiencing muscle rigidity is almost impossible or is accomplished only with great effort, despite the fact that the animal may be immobilized and anesthetized.

Mortality resulting from hyperthermia or respiratory depression is usually not an acceptable outcome from any medical or scientific study or examination. Since the animal must be released into the natural environment after completion of the examination or procedure, the animal is likely to be unable to move in response to flight-invoked stimulus or be unable to naturally protect itself if the animal remains partially sedated. Under such circumstances the animal is placed at an unacceptable risk of death or injury from its natural predators or from encountering natural environmental hazards such as cliffs and bodies of water.

A significant disadvantage of using known previous synergistic drug combinations is that the individual pharmaceutically active components are highly regulated DEA schedule II and DEA schedule III drugs. Governmental regulations govern the use of such drugs because of their potential for human abuse. Precise accounts of the volumetric quantity of the drugs used must be kept. A substantial administrative burden is involved in such accounting and other record-keeping. Governmental regulations also require legitimate users to keep the drugs secure from theft, which in practicality means that the drugs must be kept in very substantial locked safes. The record-keeping and safety regulations make actual use of substantial quantities of such prior synergistic drug combinations very difficult, and in some cases impossible during prolonged medical, physiological, morphological or herd health assessment studies carried out in the field or environment of free ranging non-domesticated animals.

Another important issue of any immobilizing and anesthetizing drug is the ability to formulate it quickly into doses of different potencies in the field, to accommodate different sizes of non-domesticated animals that may be encountered. To accomplish this, the drug must remain viable in a environment which does not permit special preservation methods and techniques, such as refrigeration. Animal studies may go on for days or weeks, and the immobilizing and anesthetizing drug must remain useful for the duration of such studies. Safety to the humans handling potent drugs is also an important concern, so that the drugs are not inadvertently taken up by humans.

SUMMARY OF THE INVENTION

This invention involves an anesthetizing and immobilizing pharmaceutical combination, its use and its manufacture, formed by a synergistic combination of the pharmaceutically active ingredients butorphanol tartrate, azaperone tartrate and medetomidine hydrochloride (BAM). BAM is potent in small volumetric quantities, which makes it very effective for anesthetizing and immobilizing free-ranging and captive non-domesticated mammalian animals. The high potency of BAM allows it to be delivered reliably, accurately and remotely by dart. A quantity of approximately 2-3 ml of BAM, or less, is sufficient to achieve complete anesthesia and immobilization, even in large animals such as 400 kg bison. BAM provides a moderate induction time, thereby reducing the amount of time required to locate the animals after administration, results in reduced travel distance by the animals before immobilization, and creates essentially universal recumbency resulting from the induced anesthesia. BAM creates superior muscle relaxation and a good anesthetic plane which greatly facilitates medical, physiologic, morphologic or herd assessment examinations. Side effects are generally minimal and acceptable. Heart rate, respiratory rate, rectal temperature, end-tidal carbon dioxide, oxyhemoglobin saturation, and indirect arterial blood pressure all remain within acceptable limits during anesthesia. Reversal of the anesthesia is straightforwardly accomplished by administering common and readily available antagonists. Recovery following administration of the antagonist is relatively rapid and smooth, thereby reducing the risks to the animals from natural environmental hazards such as predators, bodies of water and cliffs. BAM is preferably lyophilized into a stable powder form, and then reconstituted by the addition of sterile water to any potency level desired immediately before use. The relatively stable powder form of the lyophilized BAM preserves its vitality for relatively long periods of time, and minimizes risks to humans of unintentional uptake. A significant feature of BAM is that its pharmaceutically active ingredient of butorphanol tartrate is a DEA schedule IV substance, and its pharmaceutically active ingredients of azaperone tartrate and medetomidine hydrochloride are not scheduled at all. Consequently, BAM offers a substantially diminished potential for human abuse, and relatively great ease of use from an administrative burden standpoint compared to other synergistic drug combinations that are subject to much greater regulation. Use of BAM becomes considerably more convenient, and maybe even possible, in circumstances where other more highly regulated synergistic drug combinations could not be used. Despite these conveniences, the effectiveness of BAM is at least equal, if not superior, to the effectiveness of some individual and synergistic drug combinations employing more closely regulated DEA schedule II and III substances.

One specific aspect of the invention involves a method of anesthetizing and immobilizing a non-domesticated mammalian animal by injecting a liquid combination of the pharmaceutically active ingredients of butorphanol tartrate, azaperone tartrate and medetomidine hydrochloride (BAM) into the animal from a dart which is shot or projected from a position separated from the animal. Additional features relate to projecting the dart from a distance of about 70 meters, delivering by the dart a volume of the BAM combination which is no greater than 3 milliliters, constituting the liquid mixture from a lyophilized powder of butorphanol tartrate, azaperone tartrate and medetomidine hydrochloride by addition of liquid to the powder, adding the liquid to the powder in the environment in which the animal is present prior to anesthetizing and immobilizing the animal, and substantially reversing the anesthesia and immobilization of the animal by injecting the animal with antagonists of the butorphanol tartrate and the medetomidine hydrochloride.

Another aspect of the invention relates to an injectable anesthetizing and immobilizing drug for non-domesticated mammalian animals comprising a combination of pharmaceutically active amounts of butorphanol tartrate, azaperone tartrate and medetomidine hydrochloride. Additional features involve a preferred relative weight ratio relationship of the pharmaceutically active ingredients in the range of 14-55 mg/ml of butorphanol tartrate, 9-36 mg/ml of azaperone tartrate, and 5-22 mg/ml of medetomidine hydrochloride, and more preferably at the approximate relationship of 27 mg/ml of butorphanol tartrate, 18 mg/ml of azaperone tartrate, and 11 mg/ml of medetomidine hydrochloride. In general, an effective amount of the mixture is no more than 3 milliliters, even for an animal having a weight of up to approximately 400 kilograms, for example.

A further aspect of the invention relates to a method of making an injectable anesthetizing and immobilizing drug for non-domesticated mammalian animals, comprising combining predetermined pharmaceutically active quantities of solutions of butorphanol tartrate, azaperone tartrate and medetomidine hydrochloride. Additional features involve lyophilizing the combined solution as a powder, formulating the powder into an injectable liquid by the addition of a liquid such as sterile water, and formulating the injectable liquid in the environment in which the animal is present.

Other aspects and features of the invention, and a more complete appreciation of the present invention, as well as the manner in which the present invention achieves the above described and other improvements, can be obtained by reference to the following detailed description of presently preferred embodiments taken in connection with the accompanying drawings, which are briefly summarized below, and by reference to the appended claims.

DETAILED DESCRIPTION

Figure 1:
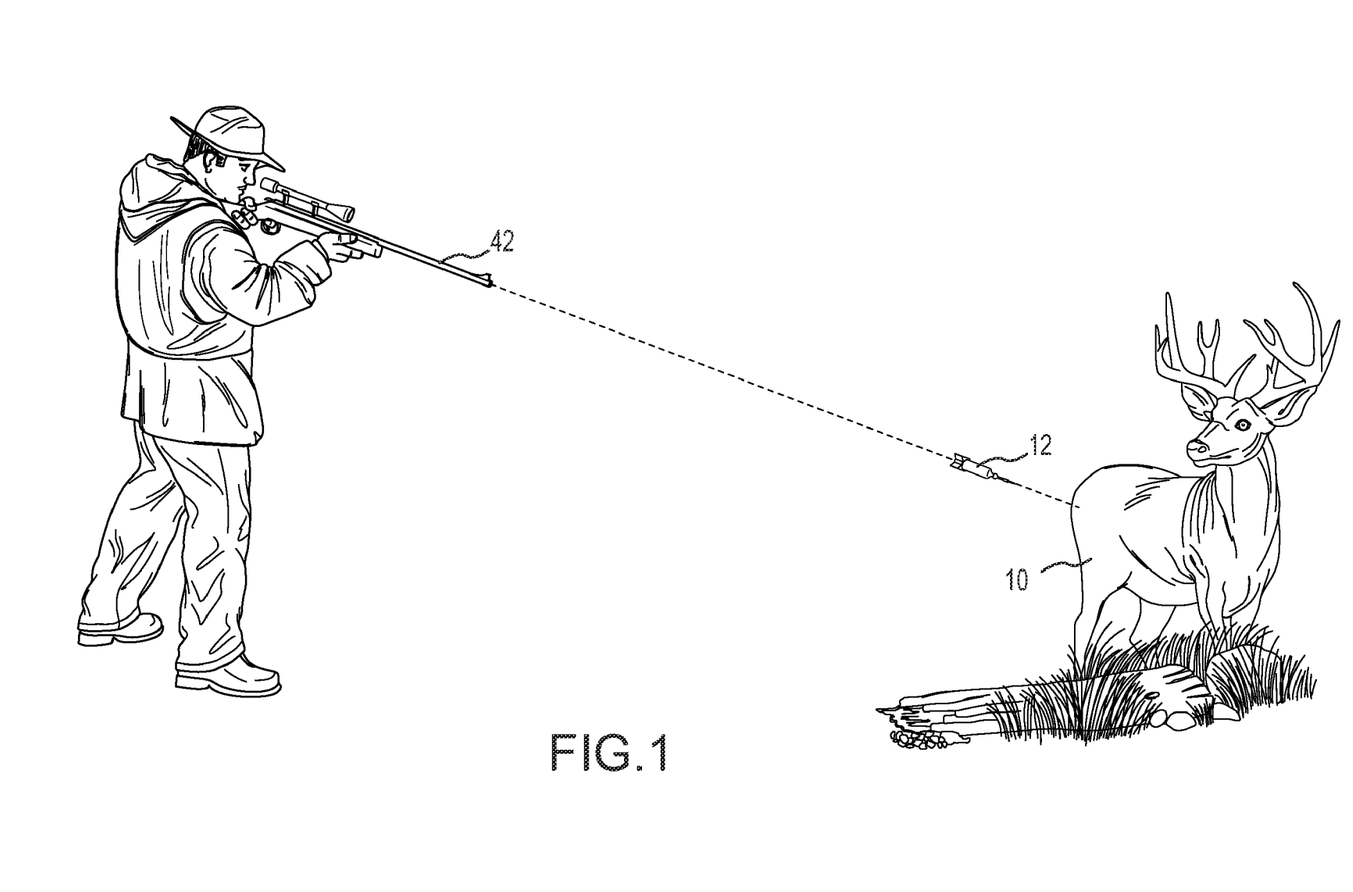
FIG. 1 is an illustration of remotely delivering an anesthetizing and immobilizing combination of pharmaceutically active butorphanol tartrate, azaperone tartrate and medetomidine hydrochloride (BAM) to a non-domesticated animal with a dart, in accordance with the present invention.
Figure 2:
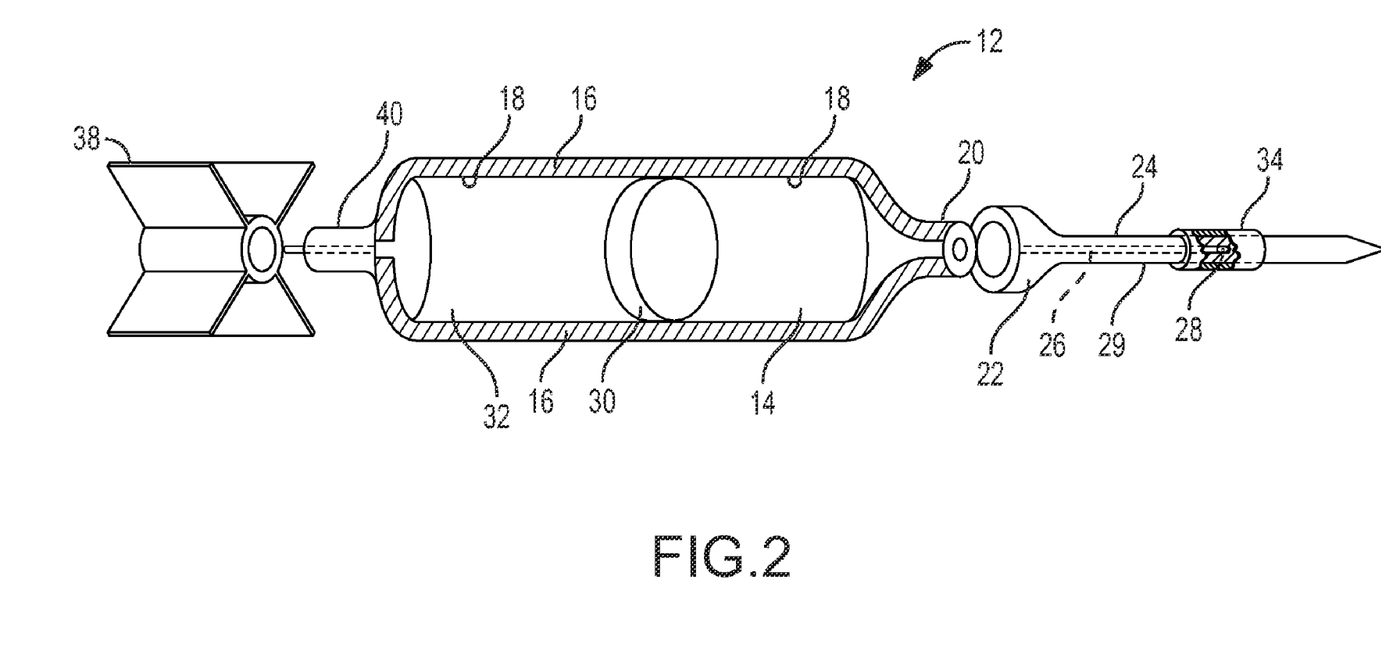
FIG. 2 is a generalized perspective view of the dart shown in FIG. 1, with portions broken away and sectioned for purposes of clarity of illustration.

The present invention involves anesthetizing and immobilizing free-ranging and captive non-domesticated mammalian animals 10, such as a deer shown in FIG. 1, by use of an anesthetizing and immobilizing combination of pharmaceutically active ingredients of butorphanol tartrate, azaperone tartrate and medetomidine hydrochloride (BAM), which is delivered remotely, preferably by a dart 12 shown in FIGS. 1 and 2. BAM is formulated as discussed below in conjunction with FIG. 3. BAM may be reconstituted as a liquid from a lyophilized powder by the addition of liquid or sterile water as shown in FIG. 4 to achieve a predetermined concentration, or BAM may be supplied as a liquid of a predetermined concentration which is ready for use.

When used as shown in FIG. 1, the weight of the animal 10 is estimated and a volumetric quantity of 3 ml or less of liquid BAM is loaded into a drug chamber 14 of the dart 12, as shown in FIG. 2. The dart is shot or projected into a muscle of the animal 10 (FIG. 1), where the BAM enters the bloodstream of the animal. After a short induction time, the BAM anesthetizes and immobilizes the animal. The animal collapses in a recumbent position, which allows the medical, physiologic, morphologic and/or herd-assessment examination, test or study to be performed.

The dart 12 used for remote delivery of the BAM is conventional. For illustrative purposes, FIG. 2 illustrates the general characteristics of a conventional dart of the type which uses compressed gas to expel the drug. The dart 12 is generally formed by a main cylindrical body 16, which also defines an interior cylindrical chamber 18 of which the drug chamber 14 is a part. A front end 20 of the main body 16 is adapted to receive a connector 22 of a hypodermic needle 24. The liquid BAM is loaded into the drug chamber 14 through the front end 20, before the hypodermic needle 24 is attached by the connector 22 to the front end 20 of the main body 16. An interior passageway 26 extends through the hypodermic needle from the drug chamber 14 to a side vent 28 in a shaft 29 of the needle 24.

A piston 30 is located in the interior cylindrical chamber 18, and separates the drug chamber 14 from an expulsion chamber 32. The expulsion chamber 32 is loaded with compressed gas or air which presses the piston 30 against the liquid BAM located in the drug chamber 14. In other types of conventional darts, a small explosive charge is located in the expulsion chamber 32, and the charge is exploded upon impact of the dart with the animal. The explosive charge provides the pressure in the explosive chamber 32. An elastomeric sleeve 34 normally covers the side vent 28 to prevent the liquid within the drug chamber 14 from escaping through the interior passageway 26 and the side vent 28 in response to the pressure on the BAM in the drug chamber 14 from the piston 30 and the compressed gas in the expulsion chamber 32. A barb 36 may be formed on the exterior of the needle 24 near its front pointed end of the shaft 29, although smooth needles 24 without barbs 36 can also be used. A stabilizer 38 is connected to the end of the main body 16 at a rear end 40 through which the compressed gas is introduced into the expulsion chamber 32. The stabilizer 38 causes the dart 12 to fly through the air in an aerodynamically improved or stabilized position with the needle 24 leading to impact the animal.

After the liquid BAM has been loaded into the drug chamber 14, and the hypodermic needle 24 with the attached sleeve 34 has been connected, the expulsion chamber 32 has been charged with compressed gas through the rear end 40, and the stabilizer 38 has been connected to the rear end 40, the dart 12 is loaded into a rifle 42, or other gun, shown in FIG. 1. The user aims the rifle 42 at the animal 10, usually from a distance which is as close as the user believes possible to approach the animal without causing flight, and the propellant used in the rifle 42 projects the dart 12 in a ballistic trajectory which contacts the animal 10 in a muscular area of the body, such as a hind quarter or shoulder.

The impact of the dart 12 with the animal causes the hypodermic needle 24 to penetrate through the hide of the animal. As the needle penetrates into the hide, the elastomeric sleeve 34 is pushed backward from the side vent 28, thereby opening the side vent 28 for the liquid BAM to flow from the drug chamber 14 through the interior passageway 26 and the side vent 28 into the muscle of the animal, in response to the pressure from the compressed gas in the expulsion chamber 32 moving the piston 30 forward in the drug chamber 14. Each barb 36 on the needle 24 holds the dart 12 in the muscle of the animal 10 long enough for the BAM in the drug chamber 14 to be injected through the side vent 28 into the animal, although the liquid BAM is expelled quickly enough that barbs 36 are not required to hold the dart in the muscle.

Once injected, the BAM is absorbed into the bloodstream of the animal from the intramuscular injection site. The BAM immobilizes the animal and causes the animal to enter into a anesthetic plane with relaxed muscles, thereby allowing manipulation of the animal during medical, physiologic, health-assessment and/or morphologic procedures and tests.

While anesthetized, the animal shows no adverse side effects which are significantly outside of the accepted norms for anesthetic parameters. The heart rate, respiration rate, rectal temperature, arterial blood pressure, and hemoglobin saturation level and other vital signs are all within normally-accepted anesthesia limits. Parameters evaluating the quality of the induction, maintenance of the anesthetic plane, muscle relaxation, anesthetic recovery, and overall anesthetic procedure are observed as favorable.

At the conclusion of the procedures and tests, the effect of the BAM is reversed by administering an antagonist formed from naltrexone, tolazoline, and atipamezole, or only by naltrexone and tolazoline, or only by naltrexone and atipamezole, depending upon the circumstances and species. Recovery is observed to be smooth and rapid, and the animal relatively quickly achieves a level of consciousness and responsiveness sufficient to guard against natural adversities such as predators, water bodies and cliffs. Significant post recovery side effects are not apparent.

Figure 3:
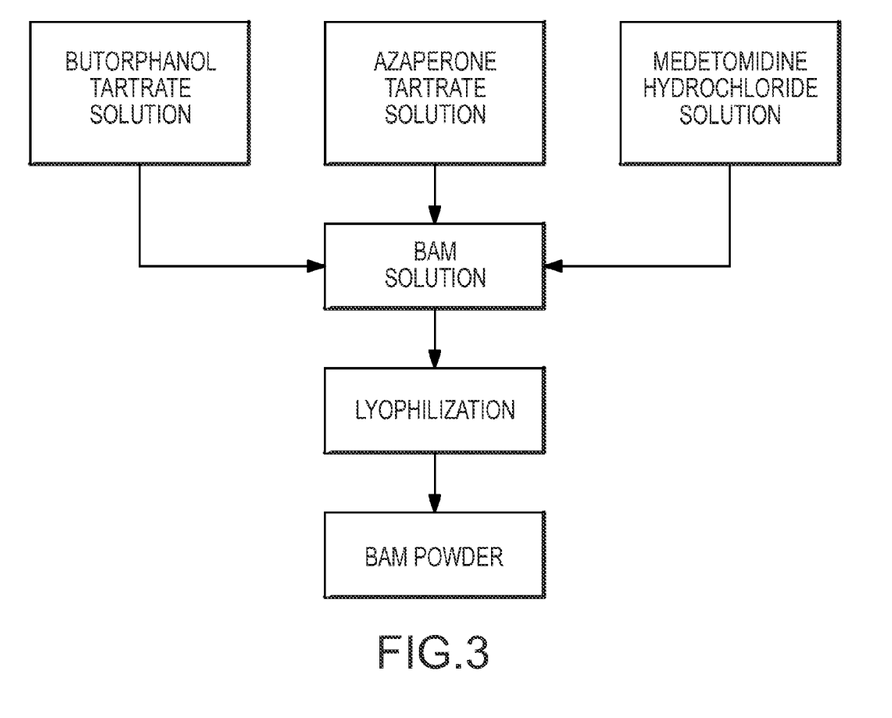
FIG. 3 is a diagram illustrating formulation of the BAM and lyophilizing the BAM into a powder, in accordance with the present invention.
Figure 4:
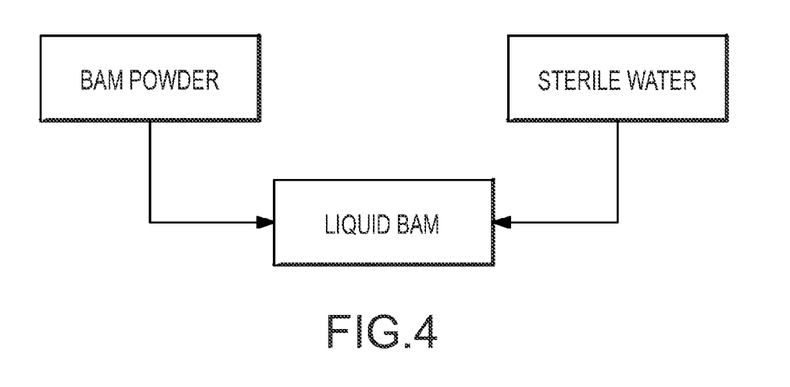
FIG. 4 is a diagram illustrating the formulation of injectable liquid BAM from BAM power, in accordance with the present invention.

BAM is prepared from solutions of butorphanol tartrate, azaperone tartrate and medetomidine hydrochloride, as shown in FIG. 3. The butorphanol tartrate solution is preferably concentrated to 50 mg/ml, the azaperone tartrate solution is preferably concentrated to 100 mg/ml, and the medetomidine hydrochloride solution is preferably concentrated to 40 mg/ml. Each solution is made separately in bulk under sterile conditions. In a single 20 ml sterile vial, 6 ml of the butorphanol tartrate concentrated (50 mg/ml) solution is added, 2 ml of the azaperone tartrate concentrated (100 mg/ml) solution is added, and 3 ml of medetomidine hydrochloride concentrated (40 mg/ml) solution is added. The resulting total solution creates a total liquid volume of 11 ml, in which there exits 300 mg of butorphanol tartrate, 200 mg is azaperone tartrate and 120 mg is medetomidine hydrochloride.

A sterile vented rubber stopper is placed on the vial by aseptic technique. The stopper is then loosened in place on the vial to allow vapors to be freely evacuated. The vial is placed in a conventional lyophilizer apparatus and its contents are rapidly cooled to minus 82° C. and held at this temperature for 30 minutes. The vials are placed inside one liter lyophilizer flasks (2 or 3 vials per flask) and the flasks connected to a conventional lyophilizer manifold. The air is evacuated and a vacuum of between 0.05 and minus 0.15 mbar is maintained for a period of at least 48 hours at ambient room temperature until the contents have reached the state of a dry powder.

Thereafter, the stoppers are pressed down hard into the vials to seal the vials, while the vials remain evacuated. The lyophilizer flasks are disconnected from the lyophilizer, and the sealed vials are removed. A metal seal is applied over the stoppers to maintain sterility and integrity. Lyophilized BAM has a substantially prolonged shelflife, but is easily reconstituted for use in the field when needed.

To reconstitute the lyophilized BAM, as shown in FIG. 4, a predetermined amount of sterile water is added to the lyophilized BAM powder to create a desired liquid concentration according to the size of the dart and the size of the animal. The concentration may be adjusted by controlling the amount of sterile water added to the lyophilized BAM powder. For example, anesthetizing and immobilizing a larger non-domesticated animal may require a higher concentration, which means that a greater amount of BAM is dissolved in a lesser amount of sterile water. In other circumstances, it may be desirable to have a greater amount of injection volume, which is achieved by increasing the amount of sterile water compared to the amount of BAM. Under typical circumstances, the usual concentration is 40 mg of total BAM components per ml of sterile water, although acceptable concentrations range from 20 mg/ml to 80 mg/ml.

Variations in the relative proportion of butorphanol tartrate, azaperone tartrate and medetomidine hydrochloride are possible, although the preferred relative weight ratio relationship of the pharmaceutically active ingredients is about 27 mg/ml of butorphanol tartrate, about 18 mg/ml of azaperone tartrate, and about 11 mg/ml of medetomidine hydrochloride. However, other suitable relative weight ratio relationships are in the range of 14-55 mg/ml of butorphanol tartrate, 9-36 mg/ml of azaperone tartrate, and 5-22 mg/ml of medetomidine hydrochloride.

The relative proportions of the pharmaceutically active ingredients butorphanol tartrate, azaperone tartrate and medetomidine hydrochloride may be varied in accordance with the response characteristics of the species and the size of animal to which the BAM is administered. Typical doses range from approximately 0.30 mg of total BAM components per kilogram of animal weight to approximately 1.30 mg of total BAM components per kilogram of animal weight. For example, a typical dose for a 50 kg white tailed deer is in the range of 1.28 mg of BAM per estimated kilogram of animal weight, while a dose of 0.31 mg/kg of animal weight may be more typical for a 300 kg elk, even though both are members of the deer (Cervidae) family. It is the responsibility of the user to make the ultimate determination of the dose.

BAM in a relatively small quantity of up to 3 ml is effective on most species of non-domesticated animals. The relatively small volumetric size of an effective amount of BAM makes delivery by a single dart from significant distances of up to 70 m very useful in achieving adequate anesthesia and immobilization, even in relatively large animals.

Reversal of the anesthesia and immobilization created by BAM is achieved by hand injection of an antagonist formed by one or more of naltrexone, tolazoline, and atipamezole. Naltrexone is effective in reversing the effect of butorphanol tartrate, and is preferably administered at approximately 2 times the butorphanol tartrate dose in terms of milligrams of butorphanol tartrate per kilogram of animal weight. Atipamezole is effective in reversing the effect of medetomidine hydrochloride, and preferably administered at approximately 5 times the medetomidine hydrochloride dose in terms of milligrams of medetomidine hydrochloride per kilogram of animal weight. Tolazoline is also effective in reversing the effect of medetomidine hydrochloride, and is preferably administered at approximately 36 times the medetomidine hydrochloride dose in terms of milligrams of medetomidine hydrochloride per kilogram of animal weight. In some circumstances, a combination of atipamezole and tolazoline may be administered to reverse the effects of medetomidine hydrochloride, in which case the relative proportions of the atipamezole and tolazoline are adjusted so that the combination does not provide a greater agonist effect than is created by the dose of medetomidine hydrochloride itself. There is no presently known effective antagonist for reversing the effect of azaperone tartrate, but azaperone tartrate creates only a mild sedative effect by itself when the synergistic effect of BAM no longer exists due to the reversal of the butorphanol tartrate and medetomidine hydrochloride. The mild and relatively short sedative effect of azaperone tartrate does not appear to create a significant risk to the animal for the relatively short amount of time that the mild sedative effect persists.

The following examples demonstrate the utility and effectiveness of the BAM in accordance with the present invention.

EXAMPLE 1

Seven female and seven male free-ranging white-tailed deer (*Odocoileus virginianus*) were anesthetized and immobilized in an approved-protocol study, by the injection of BAM administered from a single dart shot from hunting blinds stationed at deer feeding stations. Environmental temperature ranged from 11-28° C. (mean 22.2±4.1° C.). All deer were categorized as adults in good body condition.

The BAM was formulated from butorphanol tartrate at 24-40 mg/dart (30 or 50 mg/ml), azaperone tartrate at 15-20 mg/dart (50 mg/ml), and medetomidine hydrochloride at 8-10 mg/dart (20 or 40 mg/ml). Doses were based on visually estimated weights of 45.5 kg for an adult doe and 55 kg for an adult buck. Tracking was initiated a short time (approximately 5-10 min) after darting to allow drugs to reach full anesthetic effect.

Dart administration time, time to locate animal (time animal found minus time animal darted), time to recumbency (time animal recumbent minus time animal darted), time to data collection (time of initiation of data collection minus time animal darted), lag time (time of initiation of data collection minus time to recumbency) and estimated distance ran (meters), were recorded. Once located, the animal's level of anesthesia was assessed, and supplemental anesthetics administered if indicated. Once a plane of heavy sedation to light anesthesia was achieved, the time was noted as "time 0", and data collection was initiated.

Physiologic monitoring was started once the animal was secured (time 0), and continued at 5 min intervals for a 20 min period. Physiologic data collected included: heart rate (HR), respiration rate (RR), rectal temperature (T), oxyhemoglobin saturation ($SpO_2$), end tidal $CO_2$ ($ETCO_2$), and indirect arterial blood pressure (systolic arterial pressure, SAP; diastolic arterial pressure, DAP; and mean arterial pressure, MAP). Heart rate was determined by auscultation of the heart, respiration rate by counting chest excursions, and $SpO_2$ was measured using a portable pulse oximeter or a multi-parameter monitor with the sensor placed on the tongue, inguinal region, vulva, or a shaved portion of the ear. Indirect arterial blood pressure (BP) was measured in 12 anesthetic events using a blood pressure monitor or a Cardell monitor, with the cuff placed at the proximal aspect of the antebrachium of the foreleg. Rectal temperature was determined using a digital thermometer. End tidal $CO_2$ ($ETCO_2$) was determined in 11 anesthetic events using a portable capnograph or the Cardell monitor with the gas sampling port positioned at one nostril. Arterial blood samples were collected from the auricular artery into heparinized syringes at time 0, 10 min, and 20 min (three samples/animal). Blood gas samples were maintained on crushed ice and analyzed within 20-40 min of collection for measurement of blood pH, arterial partial pressure of oxygen ($P_aO_2$), and arterial partial pressure of $CO_2$ ($P_aCO_2$), corrected to the measured body temperature at each time point, and arterial oxygen saturation ($S_aO_2$), as measured by the analyzer. Blood was collected from the jugular vein and placed into EDTA and serum collection tubes for hematology and serum banking. Physical examination, dental examination, and standard morphometrics were done during the monitoring period.

Quality of induction, maintenance of anesthetic plane, muscle relaxation, anesthetic recovery, and overall anesthetic procedure were subjectively evaluated on a scale of 1-5 (1=excellent, 2=good, 3=fair, 4=poor, 5=unacceptable). Quality ratings were based on time to induction or recovery after drug administration, need for supplemental drug administration, degree of muscle relaxation (relaxed, intermittent rigidity or fasciculations, extreme rigidity or fasciculations, or responsiveness to stimuli), and induction/recovery characteristics (smooth, rough, rapid/lengthy, dangerous, complete/incomplete).

After a 20 min monitoring period, anesthesia was reversed with individual intramuscular (IM) administrations into the quadriceps muscles of naltrexone (50 mg/ml) at two times the butorphanol tartrate dose (60-100 mg/animal), and atipamezole (5 mg/ml) at five times the medetomidine hydrochloride dose (40-50 mg/animal). Recovery time (time to standing minus time of reversal agent administration) and total down time (time at standing minus time at recumbency) were recorded. The deer were immediately released to the wild following successful recovery.

For 13 of 15 anesthetic events, deer were heavily sedated to lightly anesthetized using butorphanol tartrate (0.58±0.1 mg/kg), azaperone tartrate (0.37±0.06 mg/kg), and medetomidine hydrochloride (0.19±0.03 mg/kg). Two deer were administered intravenous butorphanol supplementation to achieve light anesthesia (0.19 mg/kg; 0.12 mg/kg). Complete recovery was achieved using naltrexone (1.34±0.42 mg/kg) and atipamezole (0.93±0.14 mg/kg).

Subjective quality ratings for anesthetic induction, maintenance, muscle relaxation, recovery, and overall anesthetic event were good to excellent.

Average heart rate (range 59-66 bpm, mean 61±2.8 bpm) and respiration rate (range 24-29 bpm, mean 26±1.9 bpm) remained within physiological limits throughout the anesthetic procedures, with the exception of one animal exhibiting persistent tachypnea. Average systolic, diastolic, and mean arterial blood pressures ranged from 122-128 (124±2.3 mmHg), 66-79 (70±5.3 mmHg), and 93-110 mmHg (100±7.4 mmHg), respectively, and were relatively stable throughout the anesthetic event. Average rectal temperatures were elevated (range 39.3-39.5° C., mean 39.4±0.08° C.), but not consistent with persistent hyperthermia (T>103° F.; >39.4° C.). Bradycardia (HR<60 bpm) or tachycardia (HR>150 bpm) were not observed, and the average mean arterial blood pressure (MAP) remained above 90 mmHg and below 110 mmHg. Arterial blood gas, $SpO_2$, and $ETCO_2$ values revealed mild to moderate hypoxemia and/or mildly depressed ventilation ($SpO_2$<90%), without hypercapnea ($P_aCO_2$ and/or $ETCO_2$>60 mmHg) or acidosis (pH<7.3).

Regular monitoring of HR, RR, T, and BP at five minute intervals revealed stable parameters that remained within physiological limits throughout the anesthetic event. Persistent development of bradycardia (HR<60 bpm) or tachycardia (HR>150 bpm) did not occur. Although electrocardiograms were not performed, pathologic arrhythmias were not detected during cardiac auscultation, and heart rates were comparable to those reported for other cervid anesthesias. Only one animal exhibited persistent tachypnea (RR>50 bpm). The increased respiratory rate in this animal was attributed to poor ventilation, evidenced by the decreased $SpO_2$ and $S_aO_2$ readings. The poor ventilation was attributed to large body size (73.4 kg), poor positioning (slightly lateral recumbency), and mild-moderate bloating resulting in pressure on the diaphragm. Respiratory rate and severity of bloating decreased when the animal was re-positioned into sternal recumbency. Despite the high-normal average rectal temperatures (39.4±0.08° C.), persistent hyperthermia (T>103° F.; >39.4° C.) was not encountered. Average systolic, diastolic, and mean arterial blood pressures were comparable to values recorded in other cervid anesthesias.

Mean arterial blood gas values of BAM-anesthetized deer revealed mild hypoxemia and depressed ventilation ($SpO_{2<90}$%) but adequate oxygenation ($P_aO_2$>60 mmHg, $S_aO_2$>90%), without hypercapnea or acidemia. Average $SpO_2$ did not fall below 85 mmHg for any deer during the 20 min anesthetic event. Because $P_aO_2$ and $S_aO_2$ values were measured directly, and not calculated based on human oxygen-hemoglobin dissociation curves, they represent more accurate indicators of oxygenation status than $SpO_2$. Based on $P_aO_2$ and $S_aO_2$ values, all deer in this study were adequately oxygenated. Average $P_aCO_2$ readings remained below 60 mmHg, but were mildly elevated. In some cases, re-positioning of the animal into sternal recumbency from a more lateral position improved pulse oximetry and capnograph readings. Supplemental oxygen administration and/or intubation were not necessary or used in any deer in this study.

The overall quality of BAM anesthesia in free-ranging white-tailed deer was good to excellent, and was characterized by satisfactory induction time, induction to heavy sedation to light anesthesia, maintenance of adequate anesthetic plane and muscle relaxation for completion of all data collection and physical examination, and rapid, smooth recovery following administration of reversal agents. Despite a somewhat extended induction time, negative or life-threatening consequences such as injuries, tachycardia, bradypnea/tachypnea, hypoxemia, hyperthermia, lactic acidosis, or acute capture myopathy associated with the capture/anesthetic event were not observed.

Initiating tracking and/or locating the animal prior to full anesthetic effect often led to stimulation and movement of the animal (recumbent to standing, standing to ataxic walking). In two cases, animals could be approached, manual restraint applied, and supplemental butorphanol tartrate (0.19 mg/kg; 0.12 mg/kg) administered intravenously to induce a light plane of anesthesia. A longer time delay between dart administration and manipulation of these two animals likely could have resulted in full drug effect, and thus prevented the need for supplemental anesthetics. Allowing for additional time to pass often resulted in successful immobilization to a plane of heavy sedation or light anesthesia sufficient for animal handling without supplemental anesthetics. In the remaining 13 cases, once the animal was secured, supplemental drugs were not required, and muscle relaxation and anesthetic plane remained stable. Intramuscular administration of the reversal agents resulted in consistently smooth, rapid, uneventful recoveries, with little variation in recovery times. First signs of recovery (ear twitch, head movement, standing) occurred within an average of 3.2 min of drug administration, and deer were fully ambulatory and alert within an average of 4.5±1.5 min. In the majority of cases, deer not only stood within this time period, but were alert with a steady, rapid gait. This allowed for a rapid return to the deer's natural environment, with minimal risk of post-anesthetic predation or capture myopathy.

A wide weight range and various physiologic states of deer successfully anesthetized without negative consequence indicates a wide margin of safety for BAM, indicating that it is an excellent field anesthesia where animal weights are visually estimated prior to darting, and animals are immediately returned to the wild upon recovery.

EXAMPLE 2

Eight orphaned, yearling captive black bears and five free-ranging black bears (*Ursus americanus*) were effectively anesthetized and immobilized with BAM. The BAM was premixed with 0.5 ml of butorphanol tartrate (30 mg/ml), 0.25 ml of azaperone tartrate (50 mg/ml) and 0.25 ml of medetomidine hydrochloride (20 mg/ml) to yield a final mix of 15 mg/ml butorphanol tartrate, 12.5 mg/ml azaperone tartrate and 5 mg/ml medetomidine hydrochloride. The BAM was administered to the eight yearling captive black bears by hand injection. The BAM was administered to three of the five free-ranging black bears via hand injection after these bears were trapped, and by dart to the remaining two free ranging bears who were treed.

The total volume of drug administered was based on 0.4 ml BAM per estimated 50 pounds body weight prior to injection. Blood oxygenation and heart rate were measured in approximately 10 minute intervals with a pulse oximeter. Anesthetic induction was measured as the time to level 2 (partial sedation, ataxia), level 3 (sternal recumbency), and level 4 (lateral or sternal recumbency) measured to the nearest minute.

Atipamezole, in the amount of 5 mg/mg of medetomidine hydrochloride was given by intramuscular injection to antagonize the medetomidine hydrochloride. No antagonists were given for the butorphanol. Recovery was measured as time (minutes) to level 2R (increased respiration), level 3R (able to hold head up), and level 4R (able to stand).

Induction time to level 2 was difficult to assess in the captive bears because they often hid in a corner after injection. Mean time to level 3 was 5 min (range 2-6 min) and to level 4 was 8 min (range 5-10 min). Overall muscle relaxation and ease of handling was excellent. Oxygen saturation remained at 80% or above in all individuals without supplementation. Rectal body temperature ranged from 98.8-101.3° F. among individuals, at an average ambient temperature of 58° F. Heart rate ranged between 29-66 beats per minute (bpm). For free-ranging bears, mean time to level 2 was 6 min (range 2-9 min), level 3 was 10 min (range 3-15 min) and level 4 was 12 min (range 6-20 min).

The recovery mean time to level 2R was 4 min (Cl=1 min; range=2-5 min) and to level 3R was 13 minutes (Cl=4 min; range=7-17 min) and to level 4R was 15 min (Cl=4 min; 8-20 min). Animals were stimulated by 10 minutes post antagonist by massage and by change in body position. One animal recovered during transport and was not given antagonists.

The BAM provided excellent induction, anesthesia and recovery. Animals were relaxed, not aroused by pain stimulation (ear tagging) and breathed well (blood oxygen above 80%). With stimulation, anesthetic recovery was smooth.

EXAMPLE 3

Seven plains bison (*Bison bison*) were anesthetized and immobilized by BAM, made with concentrated butorphanol tartrate (50 mg/ml), azaperone tartrate (100 mg/ml) and medetomidine hydrochloride (40 mg/ml). The animals were approached on foot and injected with BAM from a 3 cc dart. Four bison were captive animals from a research facility and three were free-ranging wild bison. The mean dosages administered were 0.29 mg/kg for butorphanol tartrate, 0.14 mg/kg for azaperone tartrate and 0.07 mg/kg for medetomidine hydrochloride. Animals were blindfolded and maintained in sternal recumbency. The mean time to sternal recumbency was 14.4 minutes (range 10 to 18 minutes). The bison were non-responsive to stimuli, and quality of anesthesia was very good, similar to neuroleptoanalgesia. All vital signs remained within acceptable limits. Oxygen saturation varied from 75% to 96%, arterial oxygen averaged 63.8 mm Hg (range 59.7-69.3), and arterial $CO_2$ averaged 52.2 mm Hg (range 49.6-53.5). Reversal was achieved rapidly with tolazoline at a mean dosage of 3.9 mg/kg (half IV and half IM) and naltrexone 0.17 mg/kg (IM). The mean recovery time was 4.4 minutes (range 2.0-8.5 minutes).

EXAMPLE 4

BAM was administered to captive white-tailed deer (*Odocoileus virginianus*) at two dose levels (BAM-1 and BAM-2) in an approved-protocol study, to evaluate efficacy, quality of anesthesia, and quality of recovery following administration of tolazoline, atipamezole, and naltrexone antagonists.

The deer of the study were housed in large (0.4-0.8 ha) forested outdoor pens and were fed 17% protein ration with fresh hay and water available ad libitum. The average ambient temperature at time of immobilization and anesthesia was 14.4° C. Temperatures ranged from −1.7 to 25.6° C.

The deer were moved from outdoor pens 16-24 hrs before administration of the BAM and individually directed into a drop floor-type squeeze chutes equipped with an electronic scale. After obtaining body weights, each deer was moved into an individual 3×6 m barn stall where food was withheld to minimize rumenal tympany. A single hand-administered intramuscular injection (IM) of BAM consisting of 0.34 mg/kg of butorphanol tartrate (30 mg/ml), 0.27 mg/kg of azaperone tartrate (50 mg/ml), and 0.11 mg/kg of medetomidine hydrochloride (20 mg/ml), (hereinafter referred to as "BAM-1") was administered in the left hindquarter of 20 (10 male and 10 female) deer, each of which was approximately 1.5 years old. Later, 19 of the deer, and one replacement deer (a male approximately 1.5 years old), each received an IM injection of 0.30 mg/kg of butorphanol tartrate, 0.16 mg/kg of azaperone tartrate, and 0.20 mg/kg of medetomidine hydrochloride (hereinafter referred to as "BAM-2").

Immediately after BAM injection, each deer was released into a 15×20 m observation pen where the time to first noticeable drug effect (e.g., stumbling, gait changes) was recorded, the sternal time (when deer collapsed without rising again) was recorded, the lateral time (when deer lowered head and became immobile) was recorded, and the approachable time (when deer remained immobile and seemed oblivious to its surroundings) was recorded. Immobile deer were placed in a sternal position to prevent rumen bloat.

The heart rate (determined by auscultation), respiration rate (determined by thoracic movements), rectal temperature, and hemoglobin saturation level were recorded at 0, 10, and 20 minutes after recumbency. A pulse oximeter finger probe was attached to each deer's tongue and shielded from direct sunlight. Heart rate readings from pulse oximetry were compared to heart rates as determined by auscultation.

After the last set of physiologic measurements was recorded, two observers independently reported scores of three qualitative parameters evaluating induction and anesthetic performance. A quality rating score of 0-3 was assigned to each of three categories: excitability, muscle rigidity, and overall quality. Ratings for both observers were summed and reported as a combined total quality score, giving each immobilization a potential maximum quality rating score of 18. A desirable induction was defined as having a quality score of >12.

After each trial, deer were returned to individual stalls where antagonists were administered via separate IM injections. All BAM-1 treated deer and 10 BAM-2 treated deer received 50 mg naltrexone (50 mg/ml), 200 mg tolazoline (100 mg/ml), and 10 mg atipamezole (5.0 mg/ml). This formulation of the antagonist is referred to herein as "NTA-1." Ten BAM-2 treated deer (five males and five females) received 75 mg naltrexone, 300 mg tolazoline and 15 mg atipamezole. The second formulation of antagonist is referred to herein as "NTA-2."

For deer immobilized with BAM-2 and receiving NTA-1 or NTA-2, the elapsed time from antagonist injection until each deer raised its head and until each deer stood was recorded. Beginning 30 min after antagonist injection, a sedation score was assigned to each deer at 30 min intervals for 5 hours. Scores were based on the following behavioral criteria and evaluated on a scale from 5-0: 5=lateral recumbency with no sign of reversal; 4=lateral recumbency, unable to maintain an erect head, and noticeable eye or ear movement; 3=unable to stand, fairly dazed and unsteady, but able to hold head up; 2=standing with moderate ataxia, braced stance, and sometimes lowered head; 1=minimal sedation characterized by drooping eyelids; 0=no sign of sedation. Additionally, deer were monitored at 8, 12, and 16 hr after antagonist administration to monitor for signs of resedation.

Eighteen of twenty deer (90%) injected with BAM-1 were successfully immobilized and anesthetized. One female was not recumbent at 30 min post-injection. Another female was laterally recumbent and appeared approachable after injection, but when positioned for physiological monitoring, she stood. She did not collapse again during 19 min of subsequent observation. Both deer subsequently recovered normally.

All twenty deer (100%) injected with BAM-2 were effectively immobilized and anesthetized. Time to first effect was shorter for BAM-2 treated deer than BAM-1 treated deer. Times to sternal and lateral recumbency and approach did not differ between BAM-1 and BAM-2 treated deer.

Quality ratings of immobilizations were higher for BAM-2 treated deer than BAM-1 treated deer. Hemoglobin saturation, respiration, and rectal temperature of deer treated with BAM-1 or BAM-2 did not differ Heart rate was higher for BAM-2 treated deer than BAM-1 treated deer at 0, 10, and 20 min post-recumbency. For BAM-1 treated deer, heart rate was greater at 0 versus 20 min post-recumbency, trending downward over time. For BAM-2 treated deer, heart rate also trended downward over time, but differed at 0, 10, and 20 min post-recumbency. Similar time-related downward trends were observed in hemoglobin saturation for BAM-1 and BAM-2 treatments with different values at 0 and 20 min post-recumbency. Respiration rates of deer immobilized with BAM-1 and BAM-2 generally trended downward over time with five deer treated with BAM-1 and seven deer treated with BAM-2 dropping to 8-16 breaths per min at 20 min post-recumbency. Pale colored gums and mucous membranes of 5 of 18 deer (28%) immobilized with BAM-1 were indicative of bradypnea. Only 1 of 20 deer (5%) immobilized with BAM-2 had pale gums.

Hyperthermia ($\geq 41.1°$ C.) was observed in 2 of 18 deer (11%) treated with BAM-1 and 0 of 20 deer (0%) treated with BAM-2. Rectal temperatures for BAM-1 treated deer were higher at 20 min than at 0 or 10 min post-recumbency. For BAM 2 treated deer, there was no difference in rectal temperature between 0, 10, and 20 min post-recumbency.

For BAM-2 treated deer, time to head up did not differ for those receiving NTA-1 and NTA-2. Similarly, time to standing did not differ for deer receiving NTA-1 and NTA-2. No differences in mean sedation scores were detected for BAM-2 treated deer receiving either NTA-1 or NTA-2, with each deer (n=19) standing at 30 min post-injection of antagonist. However, a large tame adult male (84.6 kg, 5.5 yr old) antagonized with NTA-1 showed no signs of recovery at five hr post injection of antagonist. A subsequent IM injection of 250 mg of tolazoline was administered, which led to recovery from anesthesia, with minimal ataxia. As recovery progressed, muscle tremors and low rectal temperature (35.1° C.) were suggestive of hypothermia.

Although deer darted with BAM-1 or BAM-2 might take 13-17 minutes before entering Stage III anesthesia (unconscious with muscular relaxation and loss of reflexes), the deer would be unable to effectively walk or run in response to flight-evoked stimuli at about 8-10 min post-injection.

Normal heart rate for a deer at rest is 70-80 beats/minute. A heart rate of <30 beats/min is suggestive of heart failure and >150 beats/minute suggests other physiological problems. Heart rates for deer treated with BAM-1 or BAM-2 were well within the limits for animal welfare.

Normal respiration rate for a deer at rest is 16-20 breaths/min, but depth of respiration is equally important with deep and smooth breathing desirable. Mean respiration rates for deer in the study were acceptable.

Normal rectal temperature of deer is 35-41° C. Rectal temperatures of the deer in the study were within normal limits with the exception of two deer treated with BAM-1, which exceeded 41° C. At 20 minutes post-recumbency, mean rectal temperatures for BAM-1 and BAM-2 treated deer were acceptable.

Because deer immobilized with BAM-2 and reversed with NTA-1 or NTA-2 were standing at 30 min post-antagonist injection, with no differences in sedation scores, NTA-1 is indicated as the best choice for reversing BAM-2.

BAM-1 and BAM-2 both provided effective immobilization of captive deer. However, BAM-2 resulted in faster induction, superior anesthesia quality, and no individuals exhibiting signs of hyperthermia when compared to BAM-1. Quality of anesthesia with BAM-2 was excellent. Both BAM-1 and BAM-2 were effectively reversed by an injection of NTA-1 or NTA-2. Both NTA-1 and NTA-2 were equally effective at reversing the effects of BAM-2.

EXAMPLE 5

Eight confined and free-ranging North American elk (*Cervus elaphus*) of both sexes ranging from 4 to 18 years of age were immobilized with BAM by remote dart injection. The average body weight of these animals was 324.5 kg. The average dose rate of the BAM administered was 0.11 mg/kg of butorphanol tartrate, 0.07 mg/kg of azaperone tartrate and 0.05 mg/kg of medetomidine hydrochloride. The average time to first ataxia was 6.8 minutes. The average time to complete immobilization was 15 minutes. These animals were immobilized for periods for up to 71 minutes. After the antagonists atipamezole and tolazoline were administered, the time to complete reversal of the immobilization averaged 7.5 minutes. There were no adverse physiological parameters observed during the anesthesia.

EXAMPLE 6

Eighty five captive and free-ranging mule deer (*Odocoileus hemionus*) of both sexes ranging in age from one to 10.5 years of age were immobilized by remote dart injection with the BAM. The dose rate of the active pharmaceutical ingredients was 0.36 mg/kg of butorphanol tartrate, 0.29 mg/kg of azaperone tartrate, and 0.12 mg/kg of medetomidine hydrochloride. The average time to first ataxia averaged 4.2 minutes. Immobilization was achieved in an average time of 10.3 minutes. The immobilizations were completely reversed in an average time of 2.7 minutes by administration of atipamezole and tolazoline intravenously. The only adverse effect noted was a period of transient respiratory arrest in one animal that was pharmaceutically managed during the procedure.

EXAMPLE 7

Forty confined and free-ranging Rocky Mountain Big Horn Sheep (*Ovis canadensis*) of both sexes ranging from yearlings to 7 yrs of age were immobilized with BAM administered intramuscularly by a remotely delivered dart. The average dose rates of the individual BAM components were 0.44 mg/kg of butorphanol tartrate, 0.26 mg/kg of azaperone tartrate and 0.20 mg/kg of medetomidine hydrochloride. No more than 3 ml of BAM was required to achieve complete anesthesia and immobilization of any animal. The time to first signs of ataxia ranged from 2 to 11 minutes. The time to complete immobilization ranged from 5 to 32 minutes. The immobilization was reversed with tolazoline and atipamezole. Time to reversal ranged from 1 to 7 minutes. No mortalities were associated with the anesthesia in these 40 animals.

EXAMPLE 8

Five confined North American Pronghorn (*Antilocapra americana*) were administered BAM via remote dart intramuscular injection. The average dose rates were 0.74 mg/kg of butorphanol tartrate, 0.68 mg/kg of azaperone tartrate and 0.28 mg/kg of medetomidine hydrochloride. Induction times to ataxia ranged from 1 to 6 minutes. Time to complete immobilization ranged from 5 to 15 minutes. No adverse effects of the anesthesia were noted. The reversal time of the anesthesia using atipamezole and tolazoline was 5 minutes in three of the five pronghorns. The reversal data was not captured for the other two pronghorns.

EXAMPLE 9

Six large exotic fields consisting of two African Lions (*Panthera leo*), three Siberian Tigers (*Panthera tigris*), and One Malayan tiger (*Panthera tigris*) were administered BAM resulting in a mean dose rate of 0.159 mg/kg of butorphanol tartrate, 0.128 mg/kg of azaperone tartrate, and 0.053 mg/kg of medetomidine hydrochloride. These animals became recumbent in 4-5 minutes and reached a state of anesthesia allowing approach and manipulation in 15-20 minutes. The depth and quality of anesthesia increased over the next 15-30 minutes. The respiration was ranked as very good. Some animals did exhibit increased blood pressures but not to the point that intervention was needed. The anesthesia was reversed with atipamezole at a mean dose rate of 0.262 mg/kg and naltrexone at 0.567 mg/kg. Post recovery behavior included slight ataxia and vomiting but was not considered life threatening.

EXAMPLE 10

Sixteen white-tailed deer fawns (*Odocoileus virgianius*) of both sexes were immobilized and captured using the BAM combination delivered remotely with injection darts. The fawns were all administered 0.5 ml of the BAM combination that resulted in an average dose rate of 0.31 mg/kg of butorphanol tartrate, 0.54 mg/kg of azaperone tartrate and 0.135 mg/kg of medetomidine hydrochloride. The fawns had body weights estimated to range from 18 to 25 kg with an estimated average of 22.2 kg. Immobilization and anesthesia was achieved in an average of six minutes. The anesthesia was reversed with telazoline, atipamezole and naltrexone. The time to complete reversal was 4.5 to 5 minutes in all animals. One large male fawn had to have additional restraint of the feet with ropes due to its larger than normal size. The anesthesia was classified as good in all cases.

From an overview perspective, BAM offers significant advantages over other known synergistic drug combinations because BAM is consistent in not increasing substantially the body temperature of non-domesticated animals; BAM provides a high quality of muscle relaxation without substantially reducing the oxygen content of the blood or reducing the respiration rate and otherwise introducing significant adverse physiological responses; BAM is effectively reversed very rapidly to prevent undue harm to the animals after the anesthetic event; and BAM is formed from DEA schedule IV drugs, which makes BAM considerably easier to use because it is not subject to the administrative burden of strict record-keeping and safekeeping required for known combinations using more potent drugs. In essence, BAM achieves anesthesia and immobilization which is as good or better than any known synergistic drug combination, with no greater adverse side effects, but does so at lower costs in terms of administrative burden and responsibility.

The significance of BAM and its improvements and advantages will become apparent upon gaining a full appreciation of the ramifications and improvements of the present invention. Preferred embodiments of the invention and many of its improvements have been described with a degree of particularity. The description is of preferred examples of implementing the invention, and is not intended to limit the scope of the invention. The scope of the invention is defined by the following claims.

The invention claimed:

1. A pharmaceutical combination capable of reversibly anesthetizing and immobilizing free-ranging non-domesticated mammalian animals, consisting essentially of butorphanol tartrate, azaperone tartrate and medetomidine hydrochloride combined in solution for a single intramuscular injection having a relative weight ratio relationship of 14-55 mg/ml of butorphanol tartrate and 9-36 mg/ml of azaperone tartrate and 5-22 mg/ml of medetomidine hydrochloride.

2. A pharmaceutical combination as defined in claim 1, wherein the approximate relative weight ratio relationship of the pharmaceutically active ingredients is 27 mg/ml of butorphanol tartrate, 18 mg/ml of azaperone tartrate, and 11 mg/ml of medetomidine hydrochloride.

3. A pharmaceutical combination as defined in claim 1, wherein the injectable volume of the solution is no more than 3 milliliters.

4. A pharmaceutical combination as defined in claim 1, wherein the butorphanol tartrate, azaperone tartrate and medetomidine hydrochloride are lyophilized as a powder before injection.

5. A pharmaceutical combination as defined in claim 4, wherein the lyophilized powder is formulated into the injectable solution by the addition of sterile water.

6. A method of making the pharmaceutical combination defined in claim 1, comprising combining predetermined quantities of solutions of the butorphanol tartrate, the azaperone tartrate and the medetomidine hydrochloride.

7. A method as defined in claim 6, further comprising lyophilizing the butorphanol tartrate, the azaperone tartrate and the medetomidine hydrochloride from the solutions to form a powder.

8. A method as defined in claim 6, wherein the approximate relative weight ratio relationship is 27 mg/ml of butorphanol tartrate, 18 mg/ml of azaperone tartrate, and 11 mg/ml of medetomidine hydrochloride.

9. A method of anesthetizing and immobilizing free-ranging non-domesticated mammalian animals by injecting an effective amount of the pharmaceutical combination defined in claim 1 into the animal from a dart which is projected in a trajectory to the animal.

10. A method as defined in claim 9, further comprising projecting the dart into the animal in a trajectory of up to 70 meters.

11. A method as defined in claim 9, further comprising delivering a volume of the pharmaceutical combination to the animal which is no greater than 3 milliliters by the dart.

12. A method as defined in claim 11, further comprising injecting an animal which has a minimum weight of at least 20 kilograms.

13. A method as defined in claim 9, wherein an approximate relative weight ratio relationship of the pharmaceutically active ingredients is 27 mg/ml of butorphanol tartrate, 18 mg/ml of azaperone tartrate, and 11 mg/ml of medetomidine hydrochloride.

14. A method as defined in claim 9, further comprising constituting the solution from a lyophilized powder of butorphanol tartrate, azaperone tartrate and medetomidine hydrochloride by adding sterile water to the powder.

15. A method as defined in claim 14, further comprising adding the sterile water to the powder in the environment in which the animal is present before injecting the animal.

16. A method as defined in claim 9, further comprising substantially reversing the anesthesia and immobilization by injecting the animal with antagonists of the butorphanol tartrate and the medetomidine hydrochloride.

* * * * *